United States Patent [19]
Pelletier

[11] Patent Number: 6,139,732
[45] Date of Patent: Oct. 31, 2000

[54] CHROMATOGRAPHY COLUMN

[75] Inventor: Duane Pelletier, Oakham, Mass.

[73] Assignee: Hodge Bioseparation, Ltd., Hyde Park, Mass.

[21] Appl. No.: 09/042,547

[22] Filed: Mar. 16, 1998

[51] Int. Cl.[7] ............................................ B01D 15/08
[52] U.S. Cl. .................................... 210/198.2; 210/656
[58] Field of Search .................................... 210/635, 656, 210/659, 198.2, 198.3, 456; 95/82, 85; 96/101, 107

[56] References Cited

U.S. PATENT DOCUMENTS

| | | | |
|---|---|---|---|
| 3,966,609 | 6/1976 | Godbille et al. | 210/198 |
| 4,384,957 | 5/1983 | Crowder, III et al. | 210/656 |
| 4,752,391 | 6/1988 | Porsch et al. | 210/198.2 |
| 4,797,209 | 1/1989 | Jackson | 210/656 |
| 4,865,728 | 9/1989 | Larsson | 210/198.2 |
| 4,888,112 | 12/1989 | Kronwald | 210/198.2 |
| 4,891,133 | 1/1990 | Colvin, Jr. | 210/198.2 |
| 4,894,152 | 1/1990 | Colvin, Jr. et al. | 210/198.2 |
| 5,089,125 | 2/1992 | Hart et al. | 210/198.2 |
| 5,141,635 | 8/1992 | LePlang et al. | 210/198.2 |
| 5,188,730 | 2/1993 | Kronwald | 210/198.2 |
| 5,324,426 | 6/1994 | Joseph et al. | 210/198.2 |
| 5,366,621 | 11/1994 | Bidell et al. | 210/198.2 |
| 5,423,982 | 6/1995 | Jungbauer et al. | 210/198.2 |

*Primary Examiner*—Ernest G. Therkorn
*Attorney, Agent, or Firm*—Lahive & Cockfield, LLP

[57] ABSTRACT

A chromatography column including a column tube, a fluid distributor positioned within the column tube, and an inflatable seal positioned about the periphery of the distributor. The inflatable seal is structured to provide a fluid seal between the distributor and the column tube when inflated, without creating dead-volume within the column. The chromatography column can also include a removable and replaceable inlet tube for introducing fluid, such as the mobile phase, to the column tube. The inlet tube can include a single-piece, rigid, hollow outer tubular housing, a fluid coupling to facilitate connection to a fluid source at one of one end of the housing, and a sealing element for sealingly engaging the fluid distributor of the chromatography column at the other end of the housing. The inlet tube can also include inner liner constructed of a material that is inert with respect to the fluid introduced to the column.

17 Claims, 5 Drawing Sheets

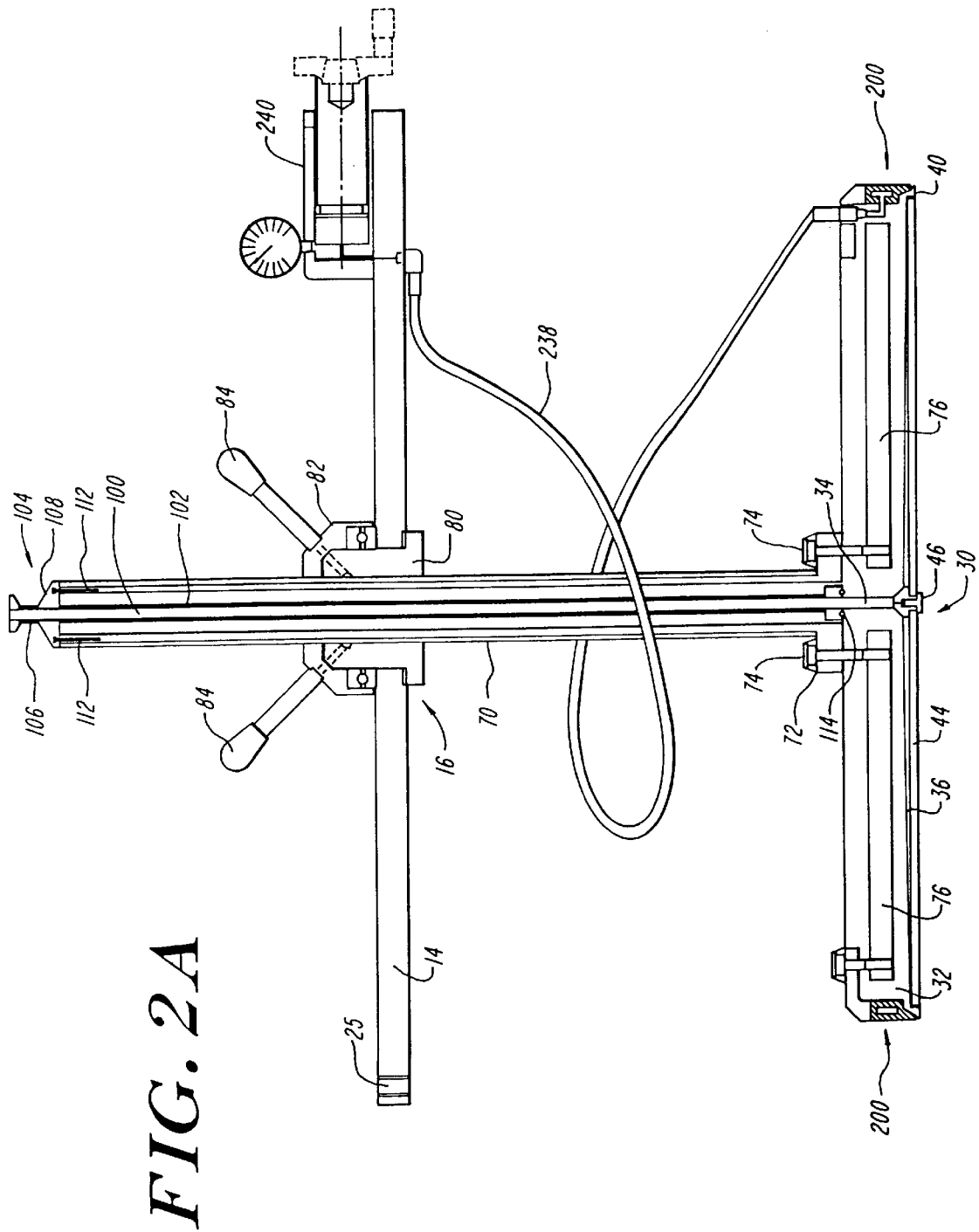

CHROMATOGRAPHY COLUMN

BACKGROUND OF THE INVENTION

The present invention relates to chromatography columns and more particularly to chromatography columns having a fluid distributor for ensuring uniform distribution of fluid across the cross-section of the column.

Chromatography columns are used for the purification, characterization, analysis, and/or preparation of molecular mixtures. Usually the column is packed with a suitable chromatographic packing material, the column is equilibrated with a suitable mobile phase (aqueous or organic), the sample is loaded onto the packing material in the column and the mobile phase is then used to selectively elute discrete molecular species.

The column serves to contain the packing material through filters usually provided at the inlet and the outlet of the column. The mobile phase enters the column through a small diameter opening at high velocity, passes through the comparatively large diameter column at a relatively low velocity, and then exits the column at a relatively high velocity through a small diameter opening. These changes in flow, cross-sectional area, and velocity make it difficult to avoid the problems presented by mixing or turbulence of the mobil phase and the presence of dead volume or stagnant areas.

Moreover, the presence of dead volume or stagnant areas within the column presents difficulties in maintaining sterile conditions within the column because microbes can become ensconced within these areas and the areas cannot be readily accessed in situ by washing of the column with a suitable sterilization solution.

The performance of chromatography separations in column configurations is dependent on the distribution (direction and velocities) of fluid into the column. The distribution of incoming fluid affects column capacity and efficiency which control the amount of materials that can be processed (throughput) and the ability to separate closely related substances (resolution).

The performance of conventional chromatography columns has proven less than optimal for a number of reasons. In particular, in columns employing a cylindrical glass enclosure, fluid leakage between fluid distributor and the glass enclosure can occur, adversely effecting the throughput and resolution of the column. Fluid leakage generally results from poor sealing between the fluid distributor and the glass enclosure due to difficulties associated with maintaining a fluid seal against a glass surface.

As the above described chromatography columns have proven less than optimal, it is an object of the present invention to provide improved chromatography columns for carrying out chromatography separation that provide ease of operation while concomitantly improving fluid distribution, throughput and, and resolution.

Another object of the present invention is to provide chromatography columns in which the amount of dead volume within the column is minimized.

A further object of the present invention is to provide chromatography columns having improved fluid sealing between the fluid distributor and the column tube.

Still another object of the present invention is to provide a chromatography column that facilitates removal and replacement of the component parts of the column.

Other general and more specific objects of this invention will in part be obvious and will in part be evident from the drawings and the description which follows.

SUMMARY OF THE INVENTION

These and other objects of the present invention are attained by the chromatography columns of the present invention which include a column tube, a fluid distributor positioned within the column tube, and an inflatable seal positioned about the periphery of the distributor. A significant advantage of the present invention over prior art chromatography columns is that the inflatable seal is structured to provide a fluid seal between the distributor and the column tube when inflated, without creating dead-volume within the column.

According to another aspect of the present invention, the chromatography column can include a pressure regulating system to inflate the inflatable seal to a desired pressure and adjust the inflation pressure of the seal. The pressurizing system allows for the adjustment of the inflation pressure of the inflatable seal to compensate for changes in the chromatography process and for irregularities in the surface of the column tube, thereby maintaining a fluid-tight seal.

According to another aspect of the present invention, the fluid distributor can include a fluid inlet, a distribution surface communicating with the fluid inlet, and a raised edge about the periphery of the distribution surface. An inner groove is preferably formed in the raised edge of the distribution surface. A porous plate can be generally centrally secured to the fluid distributor to engage the distribution surface. The porous plate includes a groove formed in the peripheral edge of the plate. A sealing member can be seated within the groove of the porous plate and the inner groove of the distributor to provide a fluid seal between the porous plate and the distributor without creating dead-volume within the fluid distributor.

According to a further aspect of the present invention, the chromatography column can include a removable and replaceable inlet tube for introducing fluid, such as the mobile phase, to the column tube. The inlet tube can include a rigid, hollow outer tubular housing, a fluid coupling to facilitate connection to a fluid source at one of one end of the housing, and a sealing element for sealingly engaging the fluid distributor of the chromatography column at the other end of the housing. Preferably, the outer tubular housing is of unitary construction.

The outer housing of the inlet tube is preferably constructed from a metal alloy such as stainless steel. The inlet tube can also include an inner liner that is preferably constructed of a material that is inert with respect to the fluid introduced to the column. For example, the inner liner can be constructed of a polymeric material, such as polypropylene, Teflon, or polyethylene, that is thermally bonded to the outer housing of the fluid inlet tube. Significant advantages of the inlet tube of the present invention are that the rigid outer tubular housing of the fluid inlet tube strengthens the inlet tube, facilitates autoclaving or sterilization of the inlet tube, inhibits fracturing of the inner liner during connection to a fluid source, and facilitates removal and replacement of the inlet tube.

BRIEF DESCRIPTION OF THE DRAWINGS

These and other features of the present invention will be more fully understood by reference to the following detailed description in conjunction with the attached drawings in which like reference numerals refer to like elements through the different views. The drawings illustrate principles of the invention and, although not scale, may show relative dimensions.

FIG. 2A is a side elevational view in cross-section of the fluid distributor of the chromatography column of FIG. 1, according to the teachings of the present invention;

DETAILED DESCRIPTION OF THE PREFERRED EMBODIMENTS

Figure 1:
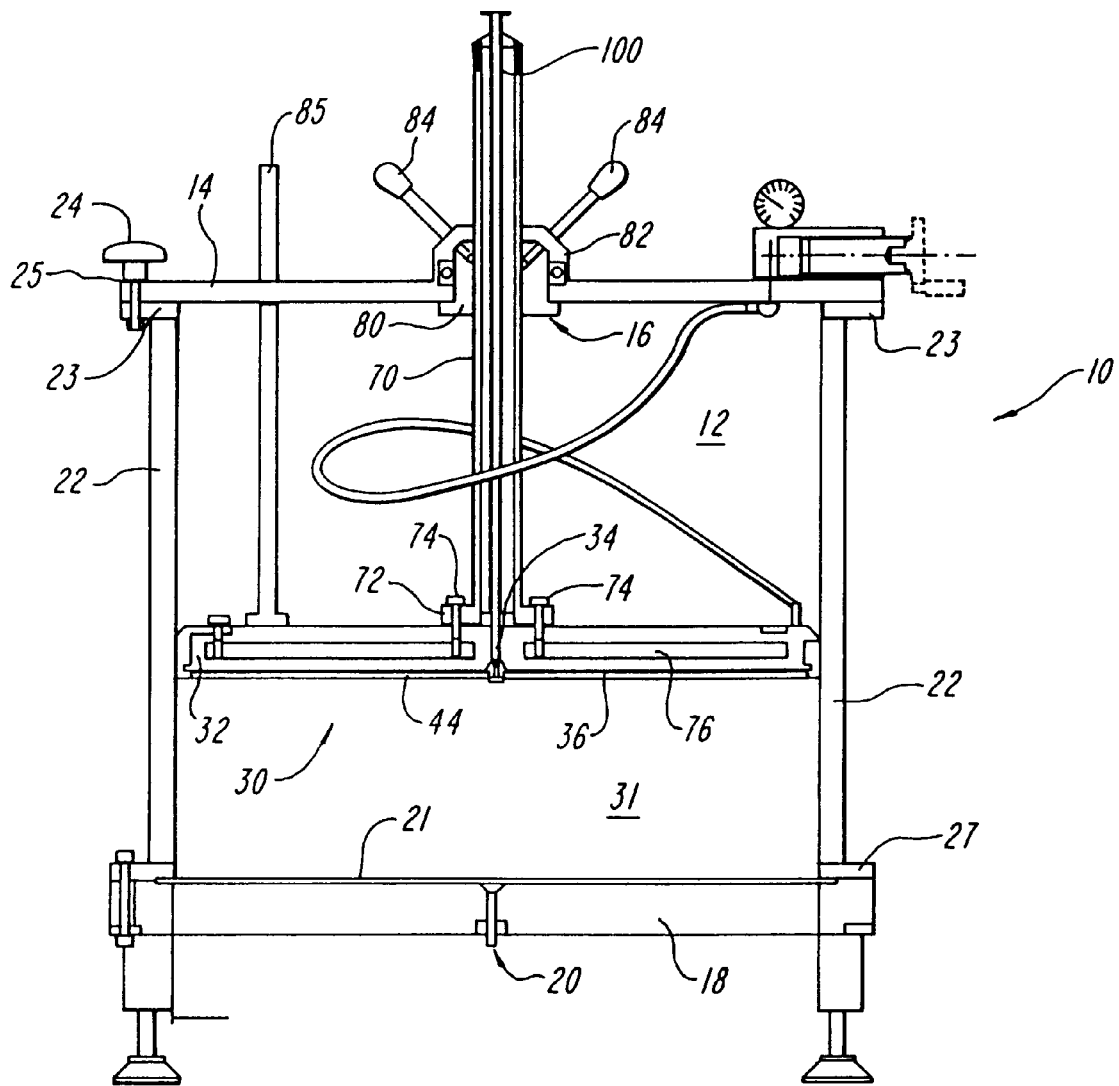
FIG. 1 is a side elevational view in cross-section of a chromatography column according to the teachings of the present invention.

A fluid chromatography column 10 for chromatographic separation of the components of a mixture is illustrated in FIG. 1. The chromatography column includes a vertically arranged glass column tube 12. A generally circular removable top plate or column cover 14 having a centrally located opening 16 is provided at the upper end of the column tube 12. A generally circular bottom plate 18 is provided at the lower end of the column 10 and includes a fluid outlet 20. A porous plate 21 is seated on the bottom plate 18 within the column tube 12. A plurality of support columns 22 are arranged about the circumference of the column tube 12 and extend between a top tube flange 23 and a bottom tube flange 27 to provide structural support to the glass column tube 12. A plurality of apertures 25 are formed in the column cover 14 about the outer circumference of the cover. A plurality of corresponding apertures are formed in the support ring 23. Screws 24 are provided to secure the column cover 14 to the support ring 23.

The term "fluid chromatography" as used herein is meant to denote chromatography systems which operate using a mobile phase, such as for example, liquid chromatography and gas chromatography, for separation of the various components of a mixture.

The column tube 12 is filled with a desired amount of packing or separation material (not shown). As is known in the art, the volume and type of packing or separation material is dependent upon the chromatography system employed.

Figure 2B:
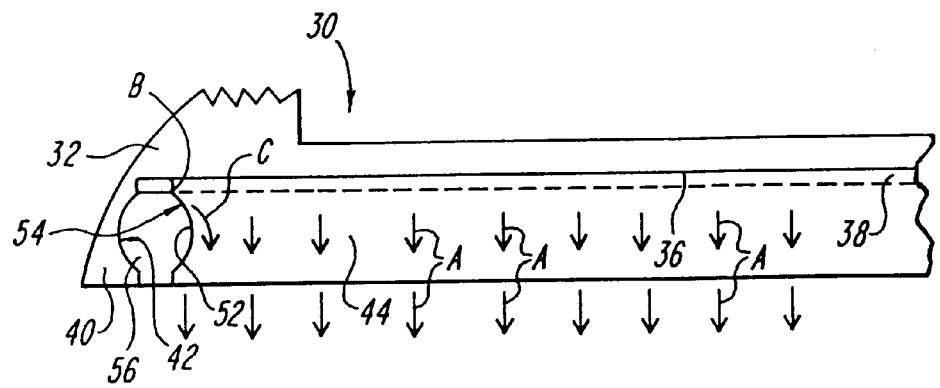
FIG. 2B is a fragmentary side elevational view of the fluid distributor, the porous plate, and the sealing member of the chromatography column of FIG. 1, according to the teachings of the present invention.

A fluid distributor 30 is positioned within the column tube 12 for evenly distributing a fluid, such as the movable phase, across the cross-section of the column tube 14, and more particularly across the cross-section of a chromatography process volume 31, as illustrated in FIG. 1. The chromatography process volume 31, within which the packing material is placed, is defined as the volume within the chromatography column 12 between the fluid distributor 30 and the bottom porous plate 21. Referring to both FIGS. 1 and 2A, the fluid distributor 30 includes a distribution plate 32 having a distribution surface 36 and a fluid inlet 34 that communicates the fluid from an inlet tube 100 to the distribution surface 36. The fluid inlet 34 is preferably located proximate the center of the distribution surface 36. The distribution plate 32 has a network of radial channels 38, as best shown in FIGS. 2B and 2C, cut into one side thereof which are designed to promote even distribution of the fluid. The channels 38 extend radially from the fluid inlet 34 to proximate an annular raised edge 40 that extends about the periphery of the distribution surface 36. Referring to FIG. 2B, an annular inner groove 42 is formed in the raised edge 40.

Referring to FIG. 2A–D, a porous plate 44, such as a frit, is secured to the distribution plate 32 and engages the distribution surface 36. A sealing screw 46 secures the porous plate 44 to a threaded gasket 48 (FIG. 2C) provided at the lower portion of the fluid inlet 34. Fluid enters the channels 38 from the fluid inlet 34 through a plurality of fluid openings 50 provided about the threaded gasket 48. A sealing groove 52 is formed in the peripheral edge 54 of the porous plate 44. A generally annular resilient sealing member 56 is seated within the sealing groove 52 of the porous plate 44 and the inner groove 42 of the distribution plate 32 to provide a fluid seal between the porous plate 44 and the distribution slate 32 while concomitantly minimizing dead-volume in the distributor 30.

Figure 2D:
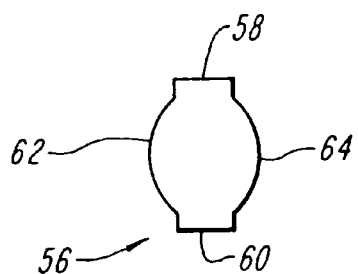
FIG. 2D is a fragmentary side elevational view in cross-section of the sealing member of the porous plate of the chromatography column of FIG. 1, according to the teachings of the present invention.
Figure 2C:
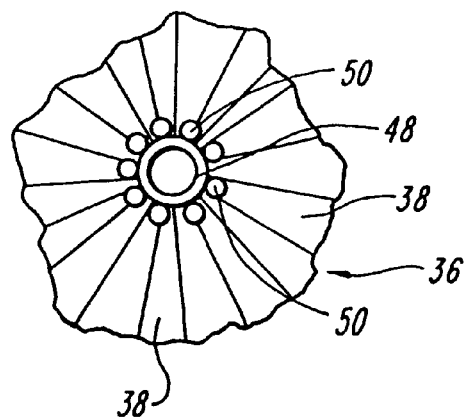
FIG. 2C is a fragmentary plan view of the distribution plate of the chromatography column of FIG. 1, according to the teachings of the present invention.

Referring specifically to FIG. 2D, the sealing member 56 includes a generally flat upper surface 58 and a generally flat lower surface 60. The sealing member 56 further includes a substantially hemispherically shaped radially outer side wall 62 that is sized and shaped to seat within the inner groove 52. Likewise, a substantially hemispherically shaped radially inner side wall 64 is sized and shaped to seat within the sealing groove 52. Preferably, the outer side wall 62 and the inner side wall 64 are symmetrical in shape.

The fluid distribution channels 38 extend from the fluid inlet 34 of the fluid distributor 30 and terminate at the sealing member 56. Fluid introduced to the fluid distribution channels 38 flows radially outward along the length of the channels. As the fluid moves along the channels 38, portions of the fluid pass through the porous plate 44 to the lower portion of the column tube 12, as indicated by arrows A in FIG. 2B. The fluid distribution channels 38 are configured to provide a radial pressure drop across the fluid distribution surface 36. The pressure drop is preferably greater at the center of the distribution surface 36 and decreases as the fluid moves radially outward through the length of the channels 38. This configuration provides for even fluid distribution throughout the length of the channels 38. The porous plate 44 provides additional back pressure to ensure even flow distribution across the fluid distribution surface 36.

At the outer radial edge of the channels 38, adjacent the sealing member 56, i.e., point B in FIG. 2B, the fluid is free to move around the sealing member 56 along the path indicated by arrow C. The gradually rounded configuration of the sealing groove 52 and the side walls of the sealing member 56 allows uninhibited fluid flow from the terminal edge of the distribution channels 38 through the porous plate 44. Accordingly, this configuration provides for even fluid distribution across the entire surface of the distribution plate 32 and the porous plate 44 while concomitantly providing a fluid-tight seal between the distribution plate and the porous plate.

A central threaded shaft 70 is fastened to the upper surface of the fluid distributor 30, as illustrated in FIGS. 1 and 2A, and forms with it a plunger or a piston which can move inside the column tube 12. This allows the position of the fluid distributor 30 to be adapted to the exact volume of the packing or separation material in the column tube 12. The central shaft 70 is a hollow cylindrical tube having a circular flange 72 at its lower end for fastening to the fluid distributor 30. A plurality of screws 74 are provided to removably fasten the central shaft 70 to the fluid distributor 30. The screws 74 extend through apertures formed in the distribution plate 32. The fluid distributor 30 can optionally include support shanks 76 for strengthening and stiffening the distribution plate 34. The support shanks 76 are preferably constructed of steel or a steel alloy, or another suitably stiff material. The use of support shanks 76 is preferable in large diameter distribution plates 32, for example over 45 cm, to inhibit warping or off-axis deflection of the distribution plate 32 as the distributor is moved within the column tube 12. When support shanks 76 are provided, it is preferable for the screws 74 to be directly threaded into the support shanks, as illustrated in FIG. 2A.

A collar 80 is provided within opening 16 of the column cover 14 and is internally threaded to receive the central shaft 70. A hub 82 is provided over the collar 80 and includes two handles 84 to aid in rotating the hub 82. The fluid distributor 30 can accordingly be raised and lowered within the column tube 12 by rotating the hub 82. A graduated anti-rotation rule 85 is fastened at one end to the top of the fluid distributor 30 and extends through an opening in the column cover 14. The anti-rotation rule 85 inhibits rotation of the fluid distributor 30 within the column. Such rotation can be caused by back pressure developed within the process volume 31 during the chromatography process. In addition, the anti-rotation rule can be used to indicate the height of the fluid distributor 30 within the column tube 12.

Figure 4:
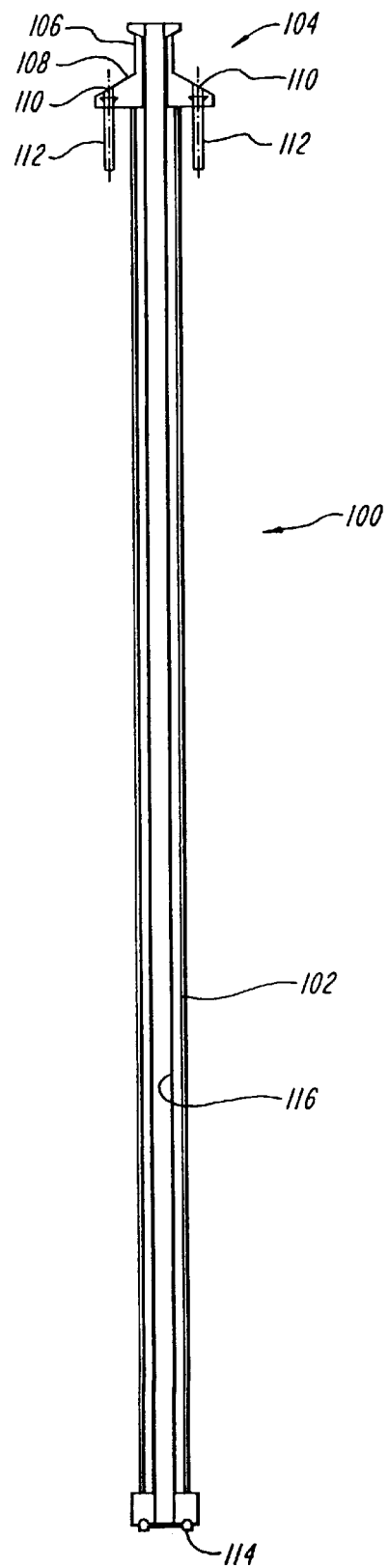
FIG. 4 is a side elevational view in cross-section of the inlet tube of the chromatography column of FIG. 1, according to the teachings of the present invention.

Referring to FIGS. 2A and 4, a removable and replaceable fluid inlet tube 100 is provided to introduce fluid, such as the mobile phase, into the column tube 12 through the fluid distributor 30. The fluid inlet tube 100 includes a rigid, hollow outer tubular housing 102 that is preferably constructed from stainless steel or another suitable metal alloy. The tubular housing 102 is preferably a single-piece, i.e. unitary construction, elongated tube that is sized to fit within the central lumen of the central shaft 70. A fluid coupling member 104 to facilitate connection to an external fluid source is provided at the upper end of the tubular housing 102. The fluid coupling member 104 includes a stainless steel neck 106 housing a sanitary fitting connection (not shown) and a tapered flange 108 having a plurality of attachment apertures 110 formed therein. The attachment apertures 110 are sized to receive screws 112 for fastening the inlet tube 100 to the central shaft 70, as best illustrated in FIG. 2A. Accordingly, a corresponding number of threaded attachment apertures are formed in the upper end of the central shaft 70 to receive the screws 112. A sealing gasket (not shown) can be employed between the flange 108 and the upper end of the central shaft 70.

The lower end of the inlet tube 100 includes a fluid sealing element 114, preferably a polypropylene sanitary gasket, for sealingly engaging the inlet tube 100 to distribution plate 32 of the chromatography column 10. The sealing element 114 is compressed into a fluid-tight arrangement with the upper surface of the distribution plate 32, about fluid inlet 34, by fastening the flange 108 to the upper end of the central shaft 70 using screws 112. Preferably, the sealing element 114 is not fastened to the fluid distributor 30 to facilitate removal of the inlet tube 100 from the column tube 12.

The inlet tube 100 can further include an inner liner 116 that is preferably constructed of a material that is inert with respect to the fluid to be introduced to the column tube 12. For example, a polypropylene inner liner is preferable for use with organic fluids, as polypropylene is generally bio-inert. Additional polymeric materials such as perflourinated polymers sold under the trademark TEFLON® copolymers by DuPont or polyurethane, can also be used. If a polymeric material is used, the polymeric liner can be thermally bonded to the interior of the tubular housing 102. The liner can also be constructed from stainless steel which is preferably welded to the interior of the tubular housing 102.

The tubular housing 102 provides rigid structural support to the inner liner 116. This is of particularly importance if the inner liner 116 is constructed of a polymeric material, as conventional polymeric liners can fracture or break when an external fluid source, such as stainless steel piping or a valve assembly is attached to the fluid inlet tube 100. Accordingly, a significant advantage of the inlet tube 100 of the chromatography column of the present invention is that it permits the use of a bio-inert polymeric liner while concomitantly providing strength and inhibiting fractures of the polymeric liner.

Moreover, the single-piece, unitary construction of the outer tubular housing 102 of the inlet tube facilitates removal and replacement of the inlet tube. The inlet tube is fastened at one, easily accessible location, the upper end of the central shaft 70, that is external to the column tube 12. Thus, the inlet tube 100 can be completely removed and replaced with minimal effort and without opening the column cover 14 or interfering with the contents of the column tube, particularly the packing material.

Figure 3A:
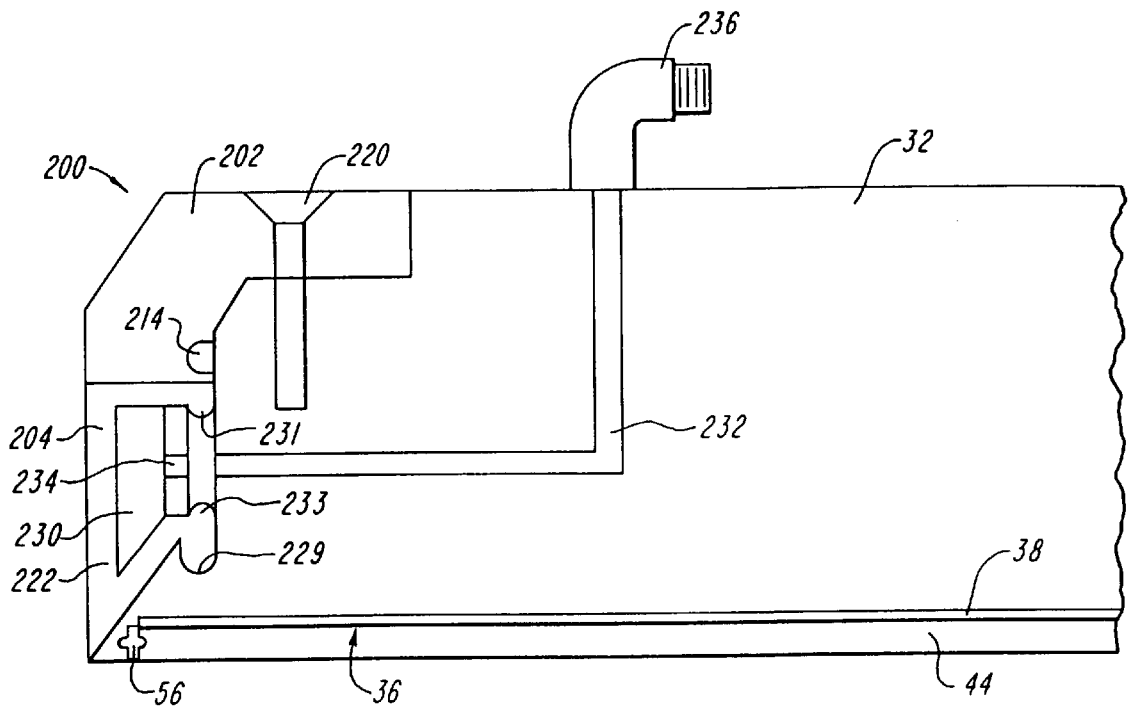
FIG. 3A is a fragmentary side elevational view in cross-section of the fluid distributor and the inflatable seal assembly of the chromatography column of FIG. 1, according to the teachings of the present invention.

The fluid distributor 30 preferably can include an inflatable seal assembly 200 for providing an adjustable fluid seal between the fluid distributor and the column tube 12, as best illustrated in FIGS. 1, 2A, and 3A. The inflatable seal assembly 200 includes a generally annular ring plate 202 that secures a tubeless inflatable seal 204 to the edge of the fluid distributor 30. Referring to FIG. 3B, the ring plate 202 includes bottom surface 206 for engaging the inflatable seal 204 and a distribution plate mating surface 218. The surface 218 includes an O-ring groove 212 for seating an O-ring 214 to provide a fluid seal between the ring plate 202 and the distribution plate 32. The ring plate 202 includes a plurality of attachment apertures 216 for receiving screws 220 to fasten the ring plate 202 to the distribution plate 32.

Figure 3C:
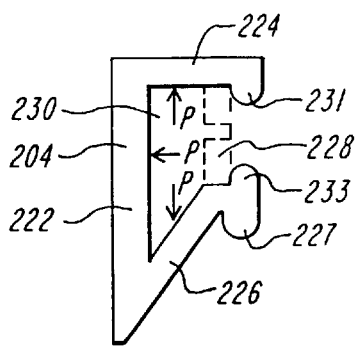
FIG. 3C is a fragmentary side-elevational view in cross-section of the inflatable seal of the inflatable seal assembly of FIG. 3A, according to the teachings of the present invention.
Figure 3B:
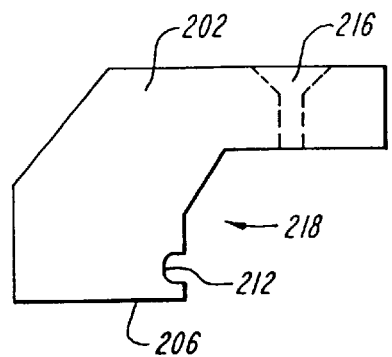
FIG. 3B is a fragmentary side elevational view in cross-section of the ring plate of the inflatable seal assembly of FIG. 3A, according to the teachings of the present invention.

Referring to FIG. 3C, the inflatable seal 204 includes a generally vertical sealing segment 222 that extends between a horizontal upper segment 224, and an angled lower segment 226. The inflatable seal 204 is preferably made of a resilient material such as EPDM. The upper segment 224 is generally complementary in shape to the bottom surface 206 of the ring plate 202. Likewise, the lower segment 226 is generally complementary in shape to the edge of the distribution plate 32. The lower segment 226 includes a resilient retaining member 227 that is sized to seat in an annular groove 229 formed around the circumference of the distributor plate. The retaining member 227 provides fluid sealing between the inflatable seal 204 and the distribution plate 32, as well as securing the seal 204 to the plate.

An annular retaining ring 228 is positioned between the upper and lower segments 224 and 226. The annular retaining ring 228 is held in place by two resilient retaining rings 231 and 233 that project from the upper segment 224 and lower segment 226, respectively, of the inflatable seal 204. The annular retaining ring 228, the sealing segment 222, the upper segment 224, and the lower segment 226 together form an annular inflation chamber 230.

A fluid conduit 232 is formed in the distribution plate 32 and communicates with the inflation chamber 230 at one end through an opening 234 provided in the retaining ring 228. A fluid fitting 236 is coupled to the other end of the fluid conduit 232. Referring specifically to FIG. 2A, a flexible tube 238 connects the fluid fitting 236 to a fluid pressure regulator 240 positioned on the column cover 14, external to the column tube 12. The fluid pressure regulator 240 is preferably a piston air pump that is in turn connected to a fluid supply through a pressure relieving regulator (not shown). Course pressure control, including reducing the fluid pressure within the inflatable seal 204, can be effected by the pressure relieving regulator. The piston air pump 240 permits fine fluid pressure control by adjustment of the piston of the air pump through rotary handle 242.

The inflatable seal 202 can be inflated by introducing a pressurized fluid, such as air, from a fluid supply to the inflation chamber 230. The pressured fluid imparts a fluid force on each of the seal segment 222, upper segment 224, and lower segment 226, as illustrated by arrows P in FIG. 3C, that operates to place the inflatable seal 204 into sealing contact with the column tube 12, the ring plate 202, and the fluid distributor 30. In this manner a fluid-tight seal can be established between the column tube 12 and the fluid distributor 30.

A significant advantage of the inflatable seal assembly 200 of the present invention is that the fluid pressure can be adjusted, through the pressure regulator 240, to compensate for changes in chromatography process conditions within the column and irregularities in the surface of the column tube 12. Such surface irregularities are particularly common in glass column tubes due to the relatively low tolerances to which the glass walls of the column are manufactured. In conventional glass chromatography columns, leakage around the fluid distributor is a common problem. Such leakage is inhibited by the inflatable seal assembly 200 of the present invention.

Moreover, the inflatable seal assembly 200 of the present invention permits adjustable sealing between the fluid distributor 30 and the column tube 12 without creating dead volume in the column tube. This results from the lower edge of the inflatable seal 204 extending to the lower edge of the fluid distributor 30 when the seal is inflated, as best illustrated in FIG. 3A. In this manner, the inflatable seal 204, the edge 40 of the distribution plate 32, and the porous plate 44 provide a substantially continuous flat surface that provides no dead volume for fluid to become trapped within.

Furthermore, this arrangement provides for an increased distribution surface 36 for the distribution plate 32, as the angled lower segment 226 permits the distribution channels 38 to extend substantially to the edge of the distribution plate 32. This results increased column throughput and resolution and reduces back pressure within the process volume 31.

Additionally, the inflatable seal assembly 200 of the present invention includes a tubeless inflatable seal 204 and thus, does not require a valve stem. Prior art seal designs incorporating a valve stem can be unreliable because the valve stem tends to wear easily, resulting in the need for frequent replacement and the potential for fluid leakage. Accordingly, the inflatable seal assembly 200 of the present invention is more reliable and wear resistant than prior art inflatable seal assemblies.

A further advantage of the seal assembly of the present invention is that the sealing pressure between the fluid distributor 30 and the column tube 12 can be objectively quantified by measuring the inflation pressure of the inflatable seal 204. In particular, the inflation pressure can be measured as the chromatography process within the process volume 31 changes to ensure consistent sealing properties between the fluid distributor and the column tube.

It will thus be seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and desired to be secured by letters patent is:

1. A chromatography column comprising
   a column tube including a cover having an opening formed therein,
   a movable fluid distributor positioned within said column tube, and
   an inlet tube passing through said opening in said column cover and engaging said fluid distributor for introducing fluid into said column tube, said inlet tube including a rigid, hollow outer housing of unitary construction, and an inner liner constructed of polymeric material bonded to said outer housing.

2. The chromatography column of claim 1, wherein said material is selected from the group consisting of polypropylene, polytetrafluoroethylene, Teflon, and polyethylene.

3. The chromatography column of claim 1, wherein said polymeric inner liner is constructed of a polymeric material which is inert with respect to the fluid introduced to said column tube.

4. The chromatography column of claim 1, wherein said outer housing is constructed from a metal alloy.

5. The chromatography column of claim 1, wherein said outer housing is constructed of stainless steel.

6. The chromatography column of claim 1, further comprising means for moving said fluid distributor within said column tube.

7. The chromatography column of claim 6, wherein said means for moving said fluid distributor is structured to receive said inlet tube.

8. The chromatography column of claim 6, wherein said means for moving said fluid distributor includes
   a hollow, threaded shaft coupled to said fluid distributor and extending through said opening in said cover, and
   a collar positioned within said opening and having a threaded opening sized to receive said threaded shaft, whereby rotation of said collar relative to said shaft effects movement of said distribution plate within said column tube.

9. The chromatography column according to claim 8, wherein said inlet tube is positioned within said hollow shaft and is fastened to an upper portion of said shaft exterior to said column tube.

10. A chromatography column comprising
    a column tube,
    a fluid distributor positioned within said column tube, said distributor including a fluid inlet, a distribution surface communicating with said fluid inlet, a raised edge about the periphery of said distribution surface, said raised edge having an inner groove formed therein, a porous plate generally centrally secured to said distributor to engage said distribution surface, said porous plate including a peripheral edge having a groove formed therein, and a sealing member seated within said groove of said porous plate and said inner groove of said distributor to provide a fluid seal between said porous plate and said distributor, said sealing member being positioned to avoid dead-volume between said porous plate, said distributor, and said seal.

11. The fluid distributor of claim 10, wherein said sealing member is a resilient annulus having generally rounded side walls and a generally flat bottom surface.

12. A chromatography column comprising a column tube, a fluid distributor positioned within said column tube, said distributor including a distribution surface, and an inflatable seal assembly including an inflatable seal positioned about the peripheral surface of said distributor, said inflatable seal being structured to provide a fluid seal between said distributor and said column tube, said inflatable seal being positioned to avoid dead-volume between said distributor, said column tube, and said seal.

13. The chromatography column of claim 12, wherein said distributor includes a fluid inlet, a distribution surface communicating with said fluid inlet, and a porous plate substantially centrally secured to said distribution plate to engage said distribution surface.

14. The chromatography column of claim 13, wherein a portion of said inflatable seal is co-planar with said porous plate.

15. The chromatography column according to claim 13, further comprising a generally annular support plate for coupling said inflatable seal to said fluid distributor.

16. The chromatography column according to claim 13, wherein said fluid distributor includes a fluid conduit formed therein for providing a fluid from a fluid source to inflate said inflatable seal.

17. The chromatography column according to claim 16, further comprising a pressure regulating system for controlling the inflation pressure of said inflatable seal.

* * * * *